United States Patent [19]
Radman

[11] Patent Number: 5,681,268
[45] Date of Patent: Oct. 28, 1997

[54] ARM SUPPORT AND CARPAL NERVE PROTECTION DEVICE

[76] Inventor: Stanley I. Radman, 59280 G.R. Treslte Ct., North Folk, Calif. 93643

[21] Appl. No.: 607,001

[22] Filed: Feb. 26, 1996

[51] Int. Cl.$^6$ ........................................ A61F 5/00
[52] U.S. Cl. .................. 602/20; 602/21; 602/19
[58] Field of Search ............... 602/4, 16, 19–21; 128/845, 874, 878

[56] References Cited

U.S. PATENT DOCUMENTS

| | | | |
|---|---|---|---|
| 9,828 | 7/1853 | Day | 602/4 |
| 2,310,566 | 2/1943 | Anderson | 602/19 |
| 3,815,588 | 6/1974 | Klausner | 602/4 |
| 4,299,210 | 11/1981 | Santy | 602/19 |
| 4,559,932 | 12/1985 | Salort | 602/20 |
| 4,628,913 | 12/1986 | Lerman | 602/19 X |
| 5,086,762 | 2/1992 | Chee | 602/4 |
| 5,411,471 | 5/1995 | Terrazas | 602/18 |

*Primary Examiner*—Linda C. Dvorak
*Attorney, Agent, or Firm*—John P. Gugliotta; David L. Volk

[57] ABSTRACT

An arm support device is disclosed similar in style to a back brace, having a back support plate connected to a pair of forward curved shoulder support plates covers the entire back and shoulders. A waist harness extends from either side of the this section to maintain its position. Two arm like segments protrude from the back side of the back support plate to the front in order for the wearer to insert his/her arms. A forearm support plate holding a wrist support glove are provided on each arm segment to help support the device to the person.

2 Claims, 5 Drawing Sheets

ARM SUPPORT AND CARPAL NERVE PROTECTION DEVICE

BACKGROUND OF THE INVENTION

1. Field of the Invention

The present invention relates generally to arm support devices and more particularly to an apparatus which may be worn to help reduce or eliminate carpel tunnel syndrome problems.

2. Description of the Related Art

In the related art, many forms of supports padding, and rehabilitation apparatus are known. For example, in U.S. Pat. No. 4,302,849, issued in the name Margetson, an arm support device is disclosed which supports the arms and is to be worn by runners to support the arms and to guide arm movements, thereby increasing running efficiency.

Also, in U.S. Pat. No. 4,627,109, issued in the name Carabelli et al., a lumbosacral support is disclosed which includes and elastic belt adapted to be worn around a person's waist and includes a Velcro fastener at its end. The padded belt as disclosed in Carabelli et al. is designed to put pressure on the supporting lumbosacral muscle on either side of the spine, while not putting pressure directly on the spinal column.

In U.S. Pat. No. 5,181,906, issued in the name Bauerfeind, a shoulder joint bandage as disclosed having an elastic sleeve for receiving the upper arm of a patient and a cap passing over the shoulder, with extension belts round and opposite vertical directions around the sleeve and cap and forming a cross over point at the apex of the cap from which the belts extend diagonally downward cross the back and chest of the patient to a lower cross over point below the armpit of the opposite arm. Such a bandage appears to be devised in order to isolate and prevent motion of the shoulder during conditions of injury or fracture.

And finally, in U.S. Pat. No. 4,862,878 issued in the name Davidson et al., an orthopedic prosthesis to aid and support the shoulder muscles during movement of the human arm is disclosed which provides a lift assistance means which makes lifting the arm a less strenuous activity of the shoulder joint.

Although documentation and reports indicate increased incidents of carpal tunnel syndrome and other repetitive motion disorders as a result of wide spread availability and use of keyboards and computer equipment, none of the above mentioned references assist in curbing frequencies of such occurrences. Consequently, a need been felt for providing an apparatus which may be worn to help reduce and even eliminate carpal tunnel syndrome problems.

SUMMARY OF THE INVENTION

It is therefore an object of the present invention to provide an improved arm support device.

It is yet another object of the present invention to provide an improved arm support device which may be worn to help reduce and even eliminate carpal tunnel syndrome problems.

It is yet another object of the present invention to provide an improved arm support device which can be light weight and worn by users while operating with computers and keyboard equipment.

It is a feature of the present invention to provide an improved arm support device which is worn covering the entire back and shoulders and provides two arm like segments in order for the wearer to insert his/her arms.

Briefly described according to the preferred embodiment of the present invention an arm support device is disclosed similar in style to a back brace, and can be constructed from carbon fiber, KEVLAR polymer fiber, nylon and silicone gel. A back support plate connected to a pair of forward curved shoulder support plates covers the entire back and shoulders. A waist harness extends from either side of the this section to maintain its position. Two arm like segments protrude from the back side of the back support plate to the front in order for the wearer to insert his/her arms. A forearm support plate and a wrist support plate are provided on each arm segment to help support the device to the person. Benefits of such a configuration are derived from the transfer of weight and stresses from the arm, shoulders and back down to the lower back and buttocks. Therefore reducing fatigue to the shoulder and back and aiding the arm to be held in the proper position thereby eliminating contact with and damage of the carpal nerve.

An advantage of the present invention is that it is lightweight and can be easily worn by a user.

Further, the primary advantage of the present invention is to aid in the support of the arms and thereby eliminate fatigue of the arms and damage to the carpel nerve thereby preventing carpel tunnel syndrome.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
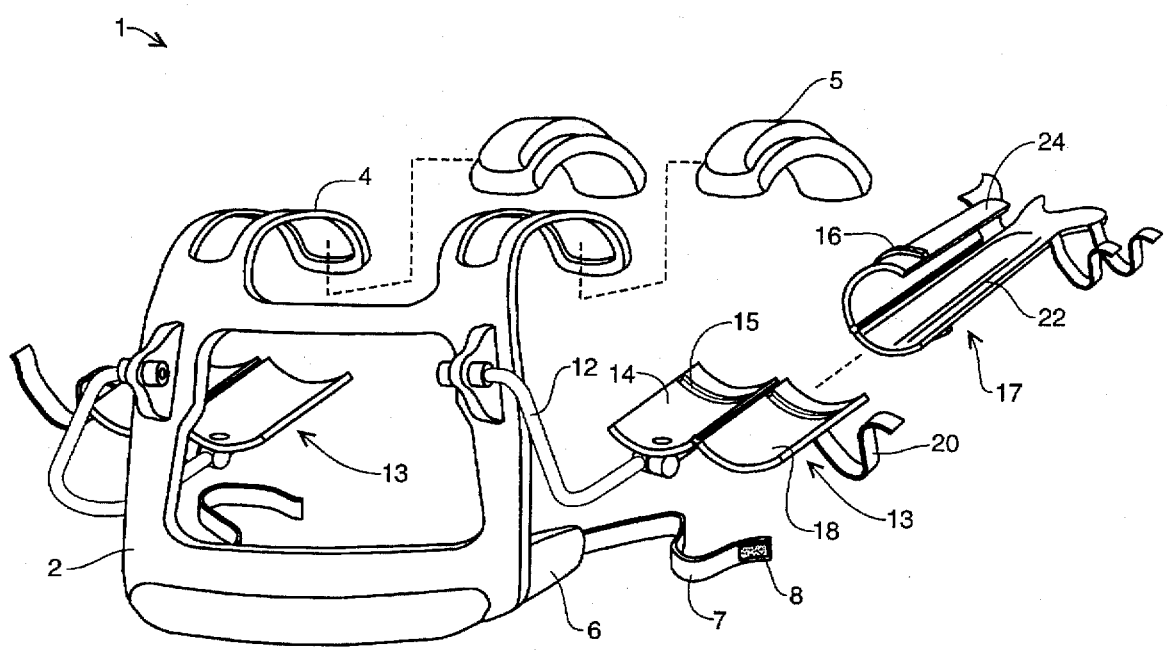
FIG. 1 is a rear prospective view of the preferred embodiment of the present invention.
Figure 2:
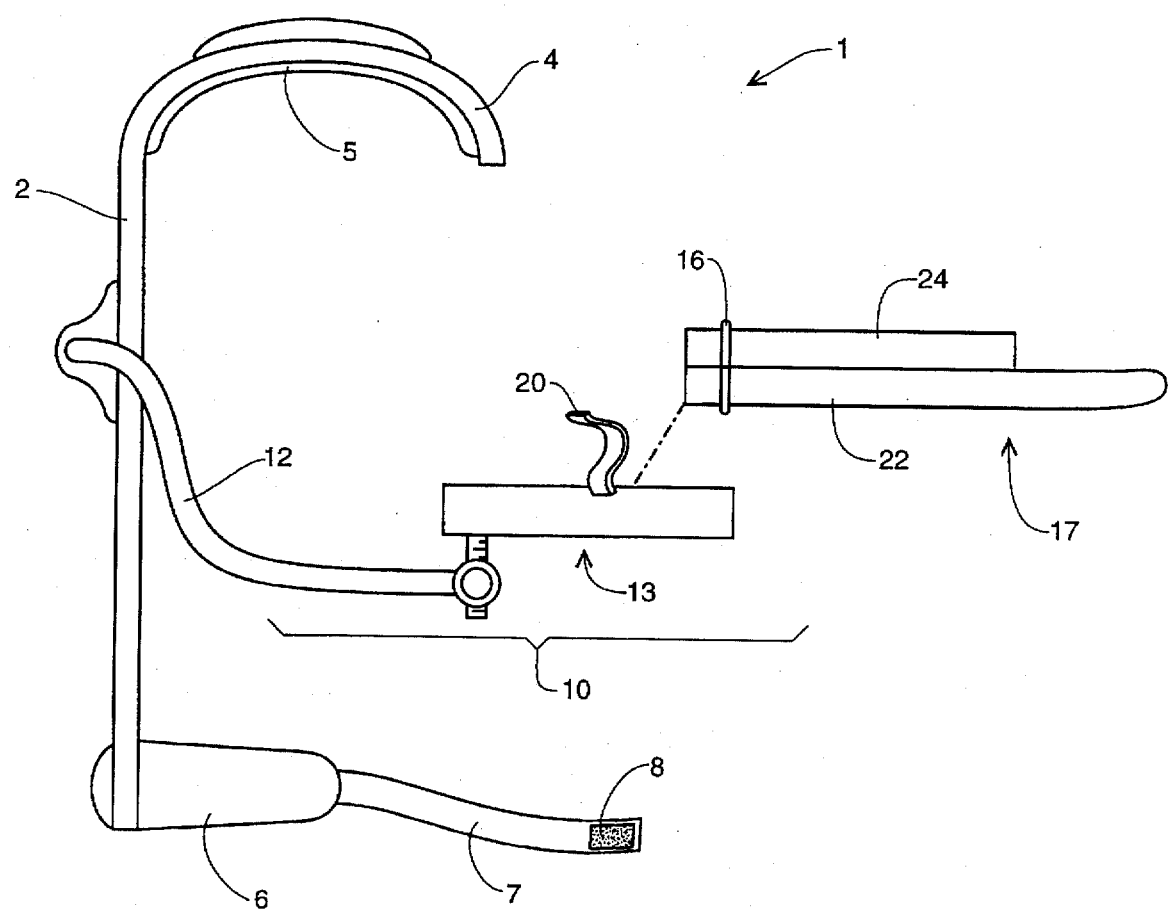
FIG. 2 is a side view thereof.

Referring now to FIG. 1 and FIG. 2, an arm support and carpal nerve protection device 1 is shown, according to the present invention, having a vertically elongated back support plate 2 topped by a pair of forward curving shoulder rest support plates 4 which each accommodate a removable shoulder pad 5. Designed to fit comfortably over an individuals shoulders, the back support plate 2 is held snugly against an individual's back via a waist harness 6 having a pair of straps 7 supporting a hook and loop fastener means 8. Although a hook and loop fastener is the preferred method of securing the straps 7 of the waist harness 6 around an individual's body, it is currently envisioned that other methods are available, such as buttons, snaps, belt-hook, or other conventional methods. Affixed at each side of the back support plate is an arm support assembly 10. Each arm support assembly 10 is comprised of an elongated, adjustable arm support bar 12 affixed pivotally to the back support plate 2. Hinged at one end of the arm support bar 12 is an upper-forearm support plate 13. Each of the upper-forearm support plates 13 comprises an elongated, curved upper-forearm resting plate 14 adapted for an upper-forearm (see FIG. 5) to rest thereon. The upper-forearm resting plate 14 is hingedly connected to an elongated, curved upper-forearm covering plate 18. The upper-forearm resting plate 14 and the upper-forearm covering plate 18 have opposing, inwardly facing, transversely formed grooves 15. Each of the upper-forearm support plates 13 includes an upper-forearm plate securing means 20 for securing the upper-forearm covering plate 18 to the upper-forearm resting plate 14 about an upper-forearm (see FIG. 5).

Figure 5:
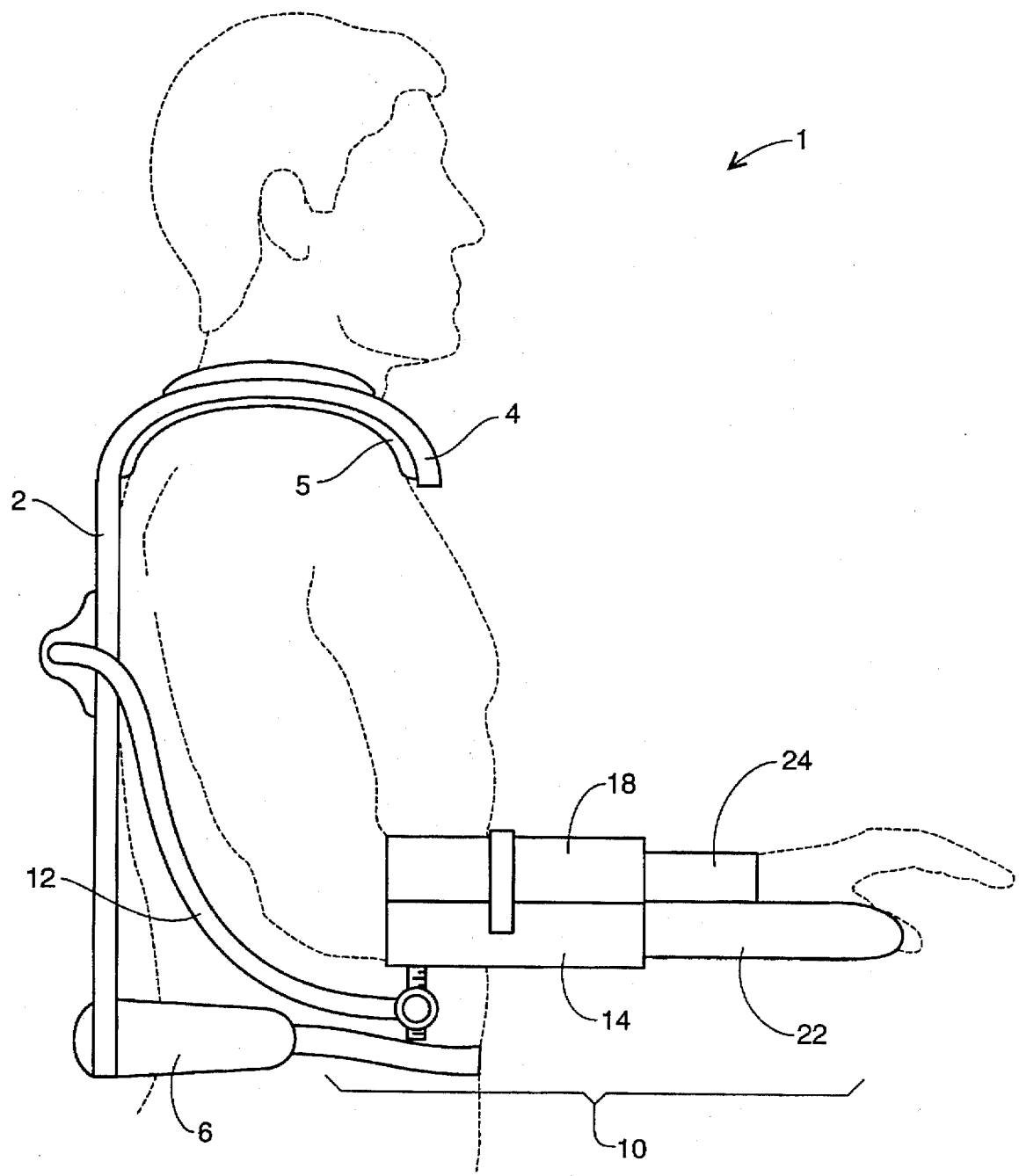
FIG. 5 is a side view of a person wearing the device described herein.

A wrist support glove 17 includes an elongated, curved lower-forearm and wrist resting plate 22 adapted for a lower-forearm and wrist to rest thereon (see FIG. 5). The lower-forearm and wristing plate 22 is hingedly connected to an elongated, curved, lower-forearm covering plate 24. The lower-forearm and wrist resting plate 22 and the lower-forearm covering plate 24 have outwardly facing, transversely formed ribs 16 configured to mate within the grooves 15 of the upper-forearm support plate 13.

Figure 3A:
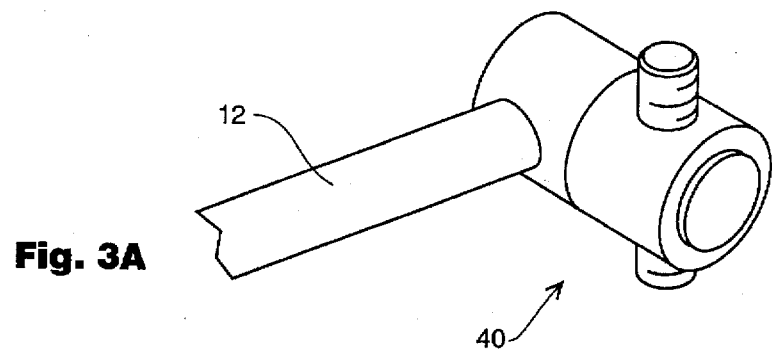
FIG. 3a is a detailed perspective view of a double pivoting swivel connection.
Figure 3B:
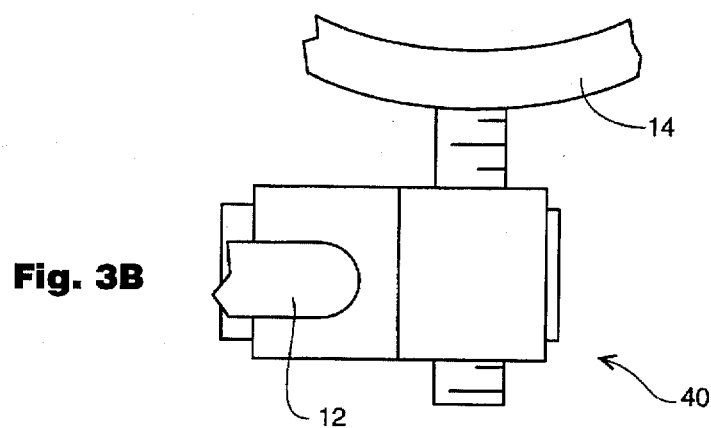
FIG. 3b is an end view thereof.
Figure 3C:
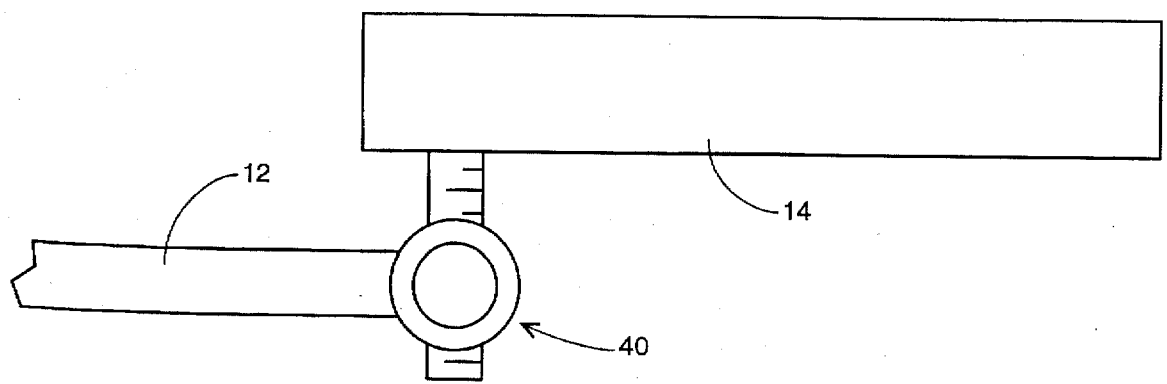
FIG. 3c is a side elevational view thereof.
Figure 4:
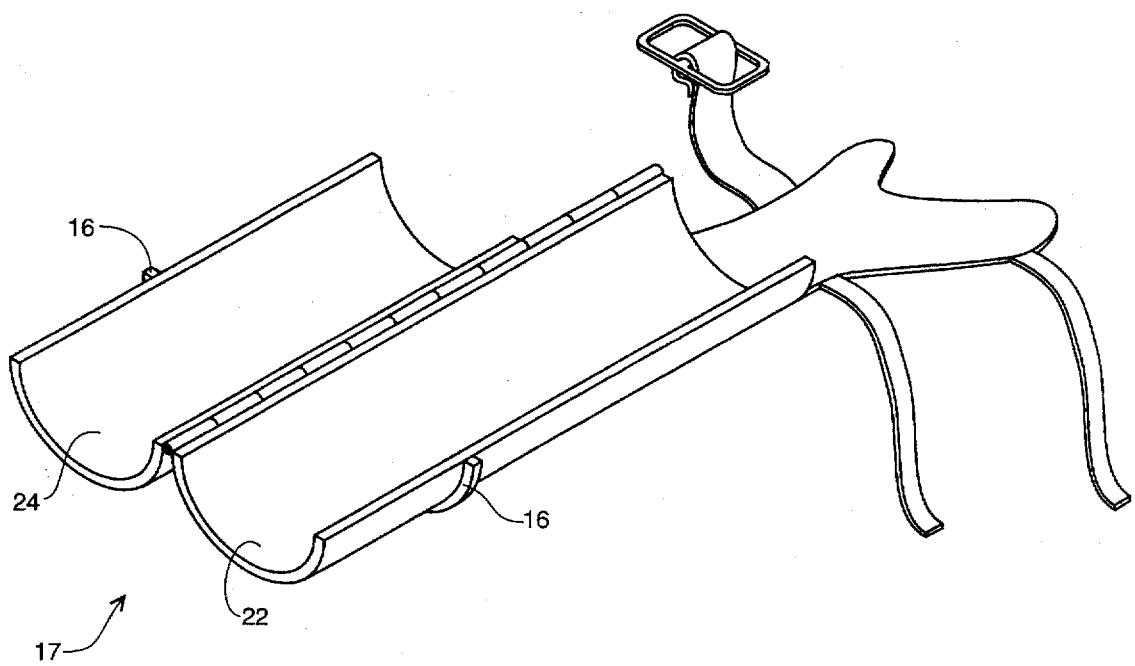
FIG. 4 is a perspective view of a wrist support glove for use with an individual arm support.

As shown in FIG. 3a, FIG. 3b, and FIG. 3c, the forearm support plate 14 is affixed to the arm support bar 12 by a double pivoting swivel connection 40. The double pivoting swivel connection 40 allows for easy adjustment of the forearm support plate 14 to accommodate normal size and mobility variations among individuals.

2. Operation of the Preferred Embodiment

In accordance with a preferred embodiment of the present invention, as shown in FIG. 5, the protective device 1 is placed over a user's shoulders, with waist harness 6 secured snugly around the user's waist. The wrist support gloves 17 are secured around an individuals wrists, and placed securely within the arm support bars 14. The pivoting swivel connections 40 are rotated into a position which is appropriate and comfortable for both the user and the task to be undertaken.

By such utilization the user will realize less fatigue, greater productivity, better posture and support, and lower incidences of irritation and inflammation of the carpal nerve.

The foregoing description is included to illustrate the operation of the preferred embodiment and is not meant to limit the scope of the invention. Many obvious and simple modifications can be made to the present invention without departing from the scope and spirit of this disclosure. Typical, but not exhaustive, of such modifications include the addition of various types of padding (silicone gel, foam rubber, etc.) at various locations, as well as utilizing various materials of construction (carbon fiber, KEVLAR polyester fiber, nylon, etc.) and manufacturing techniques. Therefore, the scope of the invention is to be limited only by the following claims.

What is claimed is:

1. An arm support and carpal nerve protection device comprising:

a back support plate having a pair of opposed sides;

an attachment means for removably affixing the back support plate to a human;

each of the sides of the back support plate having an arm support bar pivotally attached thereto;

each of the arm support bars having an upper-forearm support plate connected to a distal end thereof;

each of the upper-forearm support plates comprising an elongated, curved upper-forearm resting plate adapted for an upper-forearm to rest thereon, the upper-forearm resting plate hingedly connected to an elongated, curved upper-forearm covering plate;

each of the upper-forearm support plates comprising an upper-forearm support plate securing means for securing the upper-forearm covering plate to the upper-forearm resting plate about an upper-forearm;

a pair of wrist gloves, each of the wrist gloves having an elongated, curved, lower-forearm and wrist resting plate adapted for a lower-forearm and wrist to rest thereon, the lower-forearm and wrist resting plate hingedly connected to an elongated, curved, lower-forearm covering plate; and each of the wrist gloves comprising a connecting means for removably connecting the wrist glove to the upper-forearm support plate.

2. An arm support and carpal nerve protection device comprising:

a back support plate having a pair of opposed sides;

an attachment means for removably affixing the back support plate to a human;

each of the sides of the back support plate having an arm support bar pivotally attached thereto;

each of the arm support bars having an upper-forearm support plate connected to a distal end thereof;

each of the upper-forearm support plates comprising an elongated, curved upper-forearm resting plate adapted for an upper-forearm to rest thereon, the upper-forearm resting plate hingedly connected to an elongated, curved upper-forearm covering plate, the upper-forearm resting plate and the upper-forearm covering plate having opposing, inwardly facing, transversely formed grooves;

each of the upper-forearm support plates comprising an upper-forearm support plate securing means for securing the upper-forearm covering plate to the upper-forearm resting plate about an upper-forearm; and a pair of wrist gloves, each of the wrist gloves having an elongated, curved, lower-forearm and wrist resting plate adapted for a lower-forearm and wrist to rest thereon, the lower-forearm and wrist resting plate hingedly connected to an elongated, curved, lower-forearm covering plate, the lower-forearm and wrist resting plate and the lower-forearm covering plate having outwardly facing, transversly formed ribs configured to mate within the grooves of the upper-forearm support plate, whereby the wrist glove is removably connectable to the upper-forearm support plate.

* * * * *